United States Patent [19]

Curran

[11] 4,092,317
[45] May 30, 1978

[54] PREPARATION OF QUINOLINE DERIVATIVES

[75] Inventor: Adrian Charles Ward Curran, North Humberside, England

[73] Assignee: John Wyeth & Brother Limited, Maidenhead, England

[21] Appl. No.: 610,798

[22] Filed: Sep. 5, 1975

Related U.S. Application Data

[63] Continuation-in-part of Ser. No. 486,125, Jul. 5, 1974, Pat. No. 3,998,831.

[51] Int. Cl.² ............................................. C07D 215/20
[52] U.S. Cl. ............................ 260/283 SY; 260/289 H
[58] Field of Search ....................... 260/283 SY, 289 H

[56] References Cited

FOREIGN PATENT DOCUMENTS 1,207,930   2/1956   Germany ..................... 260/283 SY

OTHER PUBLICATIONS

Bowden, et al., J. Chem. Soc., (1946), pp. 945-948.

Sholdinov, et al., "Chem. Abstracts," 56, p. 3359b, (1962).

Elderfield, "Heterocyclic Compounds," vol. 4, pp. 36 and 37, (1952), Wiley, N.Y.

*Primary Examiner*—Donald G. Daus
*Assistant Examiner*—D. B. Springer
*Attorney, Agent, or Firm*—Arthur E. Wilfond

[57] ABSTRACT

A new process for preparing 5-oxo-tetrahydroquinolines comprises condensing a compound of formula II with a

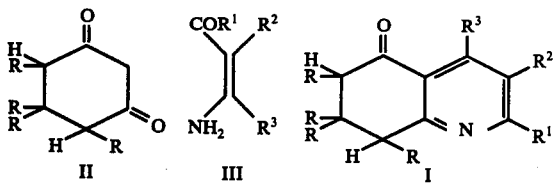

compound of formula III to obtain a compound of formula I wherein R, $R^1$, $R^2$ and $R^3$ are selected from hydrogen and lower alkyl. Compounds of formula I are intermediates for pharmaceuticals.

8 Claims, No Drawings

PREPARATION OF QUINOLINE DERIVATIVES

This application is a continuation-in-part of copending application Ser. No. 486,125 filed Jul. 5, 1974, now U.S. Pat. No. 3,998,831 in the name A. C. W. Curran and entitled: "Preparation of Quinoline Derivatives."

FIELD OF INVENTION

The invention relates to new processes for preparing 5-oxo-tetrahydroquinolines.

5-Oxo-tetrahydroquinolines are intermediates for the corresponding tetrahydroquinolines which themselves are useful for preparing pharmaceuticals such as those described in German Offenlegungschrift No. 2,352,585. I have now discovered a new route to 5-oxo-tetrahydroquinolines.

DESCRIPTION OF PRIOR ART

It is known from Breitmaier and Bayer, Angew. Chem. Internal. Edit. Volume 8, No. 10, p765 (1969) to treat cyclohexanone (2) with 3-aminoacrolein (1) to give tetrahydroquinoline as shown by the following reaction scheme This publication states that "the cyclocondensation proceeds via a Schiff base — formed between the amino group of (1) and the carbonyl group of 2 — combined with a Knoevenagel reaction between the formyl group of (1) with the methylene group of (2)."

SUMMARY OF THE INVENTION

I have now found that a 1,3-cyclohexanedione may be condensed not only with a 3-aminoacrolein but also with an alkyl 2-aminovinyl ketone to give 5-oxo-tetrahydroquinolines and further that surprisingly the condensation proceeds via a different mechanism from that predicted by the aforementioned prior art. Evidence for the different mechanism of reaction is afforded by the unexpected substitution pattern for the radicals $R^1$, $R^2$ and $R^3$ in the final products.

DETAILS OF THE INVENTION

According to the present invention there is provided a process for preparing 5-oxo-tetrahydroquinolines of formula I wherein R, $R^1$, $R^2$ and $R^3$ are the same or different and are selected from hydrogen and lower alkyl, which process comprises condensing a compound of formula II wherein R is as defined in connection with formula I with a compound of formula III wherein $R^1$, $R^2$ and $R^3$ are as defined in connection with formula I.

By the term lower alkyl is meant a straight or branched chain having from 1 to 6 carbon atoms, e.g., methyl, ethyl, n- and iso-propyl and n-, s and t-butyl. When any of R, $R^1$, $R^2$ or $R^3$ is a lower alkyl radical it is preferred that the radical has 1 to 3 carbon atoms. The term alkyl radical is also intended to embrace cyclic alkyl radicals, e.g., cyclobutyl, cyclopentyl and cyclohexyl. The R radicals may be the same or different.

The condensation of compounds of formula II and III may be achieved by heating the reactants together if desired in the presence of an anhydrous solvent, inert under the reaction conditions. Such solvents include hyrocarbon solvents with boiling points above 100° C, e.g., toluene. Glacial acetic acid may also be employed but water and alcohol solvents should be avoided. The condensation may also be effected in the presence of a catalyst, e.g., a weak base, e.g., a tri-loweralkyl-amine such as triethylamine and a salt of a weak base and a weak acid. The weak base may be ammonia, morpholine or piperidine and the weak acid acetic acid.

Preferably $R^2$ in the above formulae is methyl and preferably $R^1$ and $R^3$ are hydrogen or $R^1$ is lower alkyl, e.g., methyl and $R^2$ and $R^3$ are hydrogen.

The 5-oxo-tetrahydroquinolines may be converted to the corresponding tetrahydroquinolines by known methods.

The reaction of the present invention cannot proceed via the mechanism stated in the prior art mentioned above in view of the substitution pattern in the final products where the positions of $R^1$ and $R^3$ are reversed. Therefore, the following reaction scheme is proposed as a possible explanation of the unexpected substitution pattern in the final products.

-continued

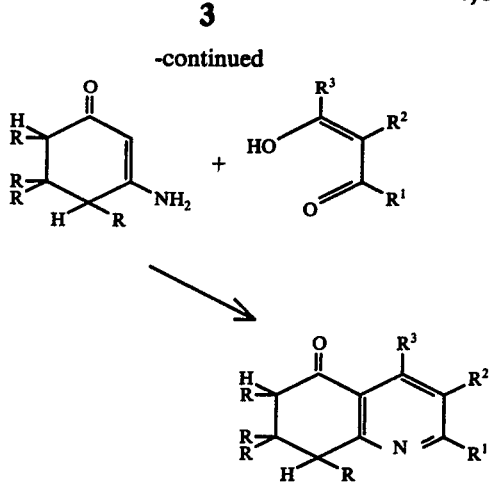

wherein R, R¹, R² and R³ are as hereinbefore defined.

The following examples illustrate the invention:

EXAMPLE 1

Preparation of 3-methyl-5,6,7,8-tetrahydroquinoline

A mixture of cyclohexane-1,3-dione (11.2 g. 0.1 m), 3-amino-2-methylacrolein (8.5 g. 0.1m) triethylamine (5 ml.) and ammonium acetate (100 mg) were heated with stirring at 120° in an oil bath for 12 hours. The cooled reaction mixture was diluted with ether (50 ml.) and the solution washed with 2N HCl (3 × 15 ml.) The combined washings were adjusted to pH 9.0 with sodium carbonate and extracted with ether (3 × 50 ml.) The combined extracts were dried, evaporated in vacuo and the residual oil distilled at 0.2 mm Hg to give the 3-methyl-7,8-dihydro-5(6H)-quinolone as a colorless crystalline solid b.p. 80° (7.5 g. 48%). A mixture of 3-methyl-7,8-dihydro-5(6H)-quinolone (20 g.), hydrazine hydrate (14 ml), diethylene glycol (150 ml.) and sodium hydroxide (14 g) was heated at reflux with stirring for 1 hour. The condenser was replaced by a Dean and Stark Water Separator and the heating continued for a further 3 hours. The cooled reaction mixture was diluted with water (200 ml.) and extracted with ether (3 × 150 ml.). The combined extracts were dried (MgSO₄) and the solvent removed in vacuo and the residual oil distilled at 15 mm Hg to give the title compound as a colourless oil b.p.116° (17 g, 93%) G.L.C. (3% SE30, T=150°) R_F=3.5 min.

EXAMPLE 2

Preparation of 3-methyl-7,8-dihydro-5(6H)-quinolone

A mixture of cyclohexane-1,3-dione (22.4 g., 0.2 mol.), 3-amino-2-methylacrolein (17 g., 0.2 mol.), triethylamine (10 ml.) and piperidinium acetate (0.25 g.) was heated with stirring in an oil bath at 120° C for 24 hours. The cooled reaction mixture was dissolved in 2N HCl (50 ml.) and extracted with ethyl acetate (3 × 50 ml.) and the organic extracts discarded. The aqueous solution was adjusted to pH 10 with sodium carbonate and extracted with chloroform (3 × 50 ml.). The combined extracts were dried (MgSO₄) and the solvent removed in vacuo. The residual oil was distilled to give the title compound as a colorless oil (17 g., 52%) b.p. 79°/0.2 mm Hg which solidified.

EXAMPLE 3

Preparation of 3,7,7-trimethyl-7,8-dihydro-5(6H)-quinolone

A mixture of 3-amino-2-methacrolein (8.5 g., 0.1 mol.) and dimedone (14 g., 0.1 mol.) was treated with triethylamine (5 ml.) and ammonium acetate (0.1 g.) and heated in an oil bath at 120° C with stirring for 20 hours. The cooled reaction mixture was diluted with 2N HCl (50 ml.) and extracted with ethyl acetate (2 × 50 ml.) and the extracts discarded. The aqueous solution was adjusted to pH 10.0 with sodium bicarbonate and extracted with ethyl acetate (3 × 50 ml.). The combined extracts were dried (MgSO₄) and the solvent removed to give a residual oil which was distilled to give the title compound as a colorless oil (7.8 g., 40% b.p. 80°/0.2 mm Hg. ($R_T$ = 2 min. 2% OV17, T=150°).

The free base was dissolved in ether and the solution treated with an excess of ethereal hydrogen chloride and the resultant solid removed by filtration, recrystallized from isopropanol to give the hydrochloride of the title compound as colorless needles m.p. 232°–235°.

(Found: C, 638.; H, 7.1; N, 6.1. $C_{12}H_{14}NO \cdot HCl$ requires: C, 63.8; H, 7.1: N, 6.2%).

EXAMPLE 4

Preparation of 2-methyl-7,8-dihydro-5(6H)-quinolone

A mixture of cyclohexane-1,3-dione (11.2 g., 0.1 mol.) and 4-aminobut-3-en-3-one (8.5 g., 0.1 mol.) was heated at 120° C, in a flask equipped for downward distillation, until the theoretical amount of water (3.6 ml.) had been obtained. The cooled reaction mixture was diluted with 2N HCl (50 ml.) and extracted with ethyl acetate (3 × 50 ml.). The aqueous phase was adjusted to pH 10.0 with sodium carbonate and extracted with ethyl acetate (3 × 50 ml.). The combined extracts were dried (MgSO₄) and the solvent removed in vacuo and the residual oil distilled to give the title compound (11 g., 68%). b.p. 65°/0.05 mm Hg. The base was dissolved in either and treated with an excess of ethereal hydrogen chloride and the resultant solid recrystallized from isopropanol to give the hydrochloride of the title compound as colorless needles. m.p. 223° C.

(Found: C, 60.7; H, 6.3; N, 6.8. $C_{10}H_{11}NO \cdot HCl$ requires: C, 60.7; H, 6.1; N, 7.1).

The substitution pattern in the pyridine ring of the title compound (free base) was proved unambiguously by analysis of its NMR spectrum in CDCl₃ solution. The NMR spectrum showed peaks due to single protons at δ = 7.12 and 8.11 pm. The coupling (J) between these protons was 8Hz.

The magnitude of this coupling (8Hz) is characteristic of couplings between H₃ and H₄ in the pyridine system — see for example: The Chemist's Companion — A Handbook of Practical Data, Techniques and References, by A. J. Gordon and R. A. Ford, Wiley-Interscience, New York, page 276 where the typical range of $J_{34}$ in pyridines is given as 6.8 to 9.1 Hz. The range given for $J_{23}$, however, is only 4 to 5.7Hz and for $J_{24}$ only 0 to 2.5 Hz. Therefore the 8Hz coupling indicates the presence of protons at positions 3 and 4 hence the methyl group must be in position 2.

I claim:

1. A process for preparing a 5-oxotetrahydroquinoline of formula I

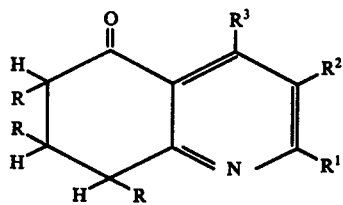

wherein R, R$^1$, R$^2$ and R$^3$ are the same or different and are selected from hydrogen and methyl which process comprises heating at about 120° C a compound of formula II

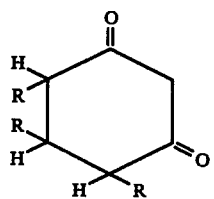

wherein R is as defined above with a compound of formula III

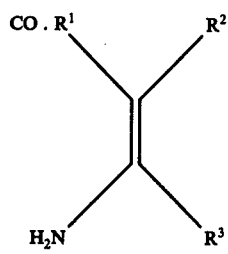

wherein R$^1$, R$^2$ and R$^3$ are as defined above.

2. A process as claimed in claim 1 wherein R$^1$ and R$^3$ are different.

3. A process as claimed in claim 1, wherein R$^3$ is hydrogen and R$^1$ is methyl.

4. A process as claimed in claim 1, wherein the reactants are heated together, if desired in the presence of an anhydrous solvent inert under the reaction conditions.

5. A process as claimed in claim 4, wherein the reactants are heated together in toluene as solvent.

6. A process as claimed in claim 4, wherein the reactants are heated together in glacial acetic acid as solvent.

7. A process as claimed in claim 1 wherein a compound of formula III is used in which R$^1$ is hydrogen, R$^3$ is hydrogen and R$^2$ is methyl.

8. A process as claimed in claim 1, wherein a compound of formula III is used in which R$^1$ is methyl, R$^2$ is hydrogen and R$^3$ is hydrogen.

* * * * *